Sept. 17, 1940. G. A. VAN ROSSEM Plant Pat. 425
ROSE PLANT
Filed May 1, 1940
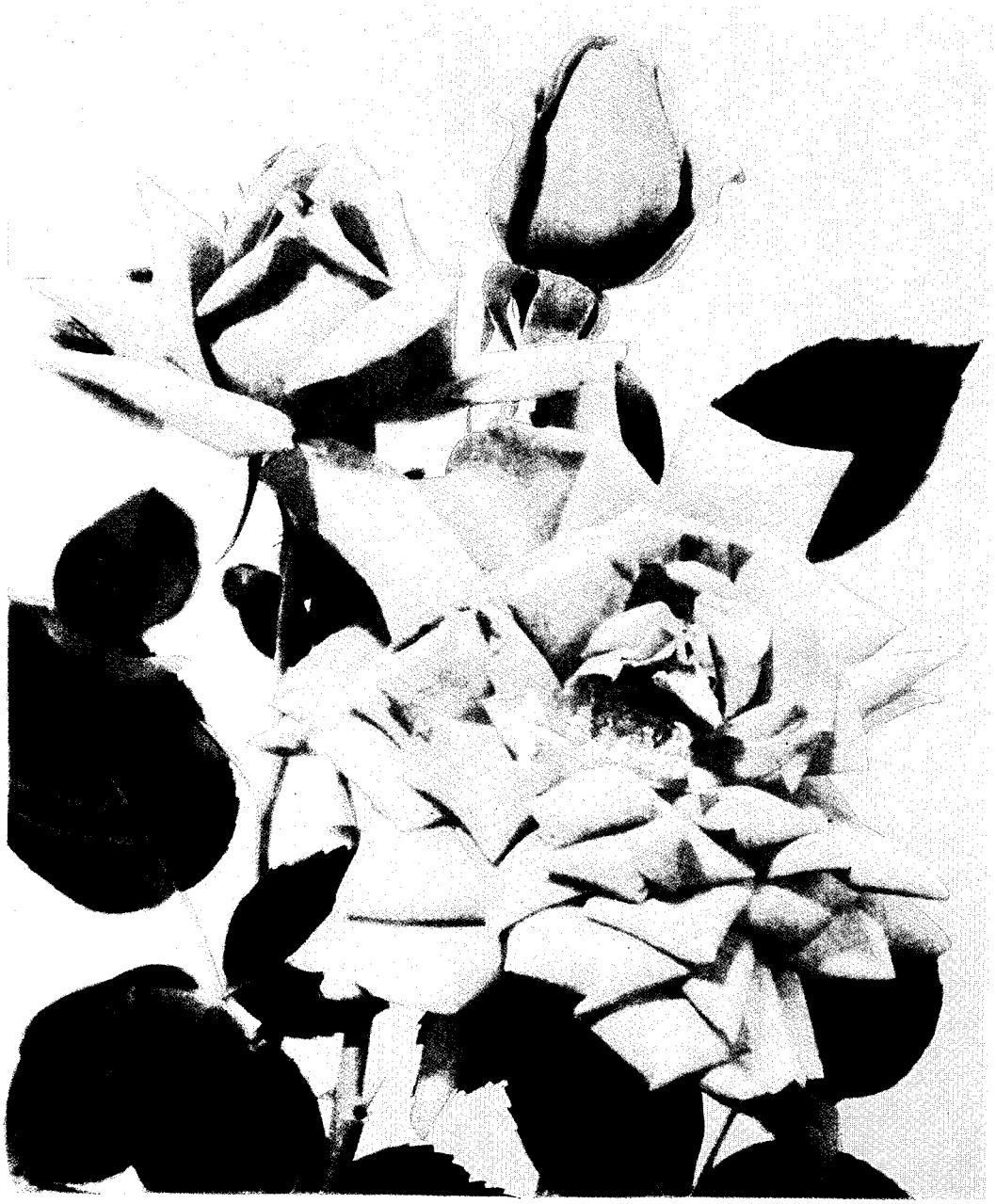
Inventor
G.A. van Rossem
By Robert Robb
Attorneys Patented Sept. 17, 1940

Plant Pat. 425

UNITED STATES PATENT OFFICE

425

ROSE PLANT

Gerard Adriaan van Rossem, Naarden, Netherlands, assignor to Jackson & Perkins Company, Newark, N. Y.

Application May 1, 1940, Serial No. 332,821

1 Claim. (Cl. 47—61)

This invention relates to a new and distinct variety of Hybrid Tea Rose plant, resulting from a cross between two well known and very attractive roses, (Charles P. Kilham x Margaret McGredy), possessing in themselves highly desirable characteristics in form and color.

The new variety is distinctively different from either of its parents and is characterized as to novelty by the attractive development of color of its blossom ranging from brilliant Carmine in the bud to Spectrum Red in the full blown flower, and the blending of the color tone of the outside petals into that of the center petals of the flower as more specifically described hereinafter.

A further feature of distinctiveness resides in the petal reflexing form of the half open flower and the similar characteristic of the fully open flower, in which each petal curls back as it develops and exposes when fully open, the nest of aniline yellow stamens.

This new rose also possesses the very desirable habit of vigorous and compact growth, with abundance of foliage.

The following is a detail description of this new variety, the color terminology being in accordance with Ridgway's Color Standard:

Parentage:
*Seedling*—
Seed parent—Charles P. Kilham.
Pollen parent—Margaret McGredy.

Classification:
Botanic and commercial—Hybrid Tea.

*Flower*

(Observations made at Newark, New York, in the morning of September 12, 1939.)

Blooming Habit:
Recurrent—Continuous.

Bud:
*Size*—Medium.
*Form*—Ovoid.
Is not affected by wet or hot weather.
*Color:*
When sepals first divide—Carmine, Plate 1.
When petals begin to unfurl—Between Pomegranate Purple, Plate 12, and Carmine, Plate 1.
When half blown—
Inside of petals—Between Carmine, Plate 1, and Spectrum Red, Plate 1.
Reverse of petals—Between Carmine, Plate 1, and Pomegranate Purple, Plate 12.

*Sepals*—Branched "hood" above bud.
Color—Malachite Green, Plate 32.
Curl back immediately after dividing.
Inside of sepals—Mineral Gray, Plate 47.

*Calyx:*
Shape—Funnel.
Size—Small.
Aspect—Smooth.
Odor when rubbed—None.
Color—Jade Green, Plate 31.

*Peduncle:*
Length—Short.
Aspect—Prickly.
Color—Light Cress Green, Plate 31.
Strength—Bending, slender.

*Opening:*
Bud opens well.
Is not affected by adverse conditions.

Bloom:
*Size*—Large.
Average when fully expanded—5".
*Borne*—Several together.
*Stems*—Medium length; strong.
*Form:*
When first open—Globular.
Permanence—Flattens; outer petals curl back.
*Petalage*—One row of petals, 4 to 6; very double (many petals and stamens hidden). Number of petals under normal conditions—45.
*Color:*
Center of flower—Between Spectrum Red, Plate 1, and Rose Red, Plate 12.
Outer petals—Rose Red, Plate 12.
Base of petals (aiglet)—Amber Yellow, Plate 16.
Inside of petals—Top third between Rose Red, Plate 12, and Tyrian Rose, Plate 12.
Reverse of petals—Rose Red, Plate 12, Amber Yellow, Plate 16, aiglet follows veins one-third length of petal.
General tonality from a distance—Rose Red, Plate 12, suffused with Scarlet Red, Plate 1.
*Variegations*—Some of inside petals show Picric Yellow, Plate 4; stripe along mid-rib.
*Discoloration:*
General tonality at end of first day—Rose Red, Plate 12, suffused with Scarlet Red, Plate 1.
Second day—Rose Red, Plate 12.
Third day—Between Rose Red, Plate 12, and Tyrian Rose, Plate 12.

Petals:
*Texture*—Thick.
Is not affected by wet or hot weather.
*Appearance:*
Inside—Velvety.
Outside—Satiny.
*Form*—Oval.
*Arrangement*—Irregular.
Petaloids in center—Few, small.
*Persistence*—Drop off cleanly.
*Fragrance*—Moderate.
Nature—"Old Rose perfume" (Centifolia).
*Lasting quality:*
On the plant and as cut flower—Long.
Genital organs:
*Stamens, Anthers*—Medium size, many.
Color—Aniline Yellow, Plate 4.
Arrangement—Regular around styles.
*Stamens, Filaments (Threads)*—Long.
Color—Apricot Yellow, Plate 4.
*Pollen*—Buff Yellow, Plate 4.
*Styles*—Uneven, medium length, thin.
*Stigmas*—Light Cadmium.
*Ovaries*—All enclosed in calyx.
Fruit:
Variety has not seeded.

*Plant*

Form:
Bush.
Growth:
Vigorous.
Foliage:
5–7 leaflets.
*Size*—Medium.
*Quantity*—Abundant.
*Color:*
New Foliage—
*Upper side*—Acajou Red, Plate 13, edges; Jade Green center, Plate 31.
*Under side*—Madder Brown edges, Plate 13; Rainette Green, Plate 31, center.
Old Foliage—
*Upper side*—Cress Green, Plate 31.
*Under side*—Light Cress Green, Plate 31.
*Shape*—Oval pointed.
*Texture:*
*Upper side*—Corrugated.
*Under side*—Smooth.
*Ribs and veins*—Prominent.
*Edge*—Serrated (saw toothed).
*Serration*—Single, small.
*Rachis*—Cress Green, Plate 31.
Under side—Prickles.
*Stipules*—Short, smooth.
*Disease Resistance*—Resistant.
Wood:
*New wood:*
Color—Light Cress Green, Plate 31.
Bark—Smooth.
*Old wood:*
Color—Cress Green, Plate 31.
Bark—Smooth.
Thorns: (Thorns are divided into thorns, prickles and short needles.)
*Thorns:*
*Quantity*—On main stalks from base and on laterals from stalk—Ordinary.
*Form*—Broad base; long, hooked downward.
*Color when young*—Lime Green, Plate 31.
*Position*—Irregular.

I claim:

A new and distinct variety of rose plant characterized as to novelty by its vigorous and compact growth with abundance of foliage, the attractive, brilliant coloring of the flower, changing as the flower develops from bud to full blown stages, and the petal reflexing habit in both said stages, substantially as shown and described.

GERARD ADRIAAN VAN ROSSEM.